(12) United States Patent
Auth et al.

(10) Patent No.: US 8,052,677 B2
(45) Date of Patent: *Nov. 8, 2011

(54) TRANSSEPTAL LEFT ATRIAL ACCESS AND SEPTAL CLOSURE

(75) Inventors: David C. Auth, Kirkland, WA (US); Robert L. Barry, Kirkland, WA (US); Robert S. Schwartz, Rochester, MN (US); Robert A. Van Tassel, Exelsior, MN (US)

(73) Assignee: CoAptus Medical Corporation, Seattle, WA (US)

( * ) Notice: Subject to any disclaimer, the term of this patent is extended or adjusted under 35 U.S.C. 154(b) by 1207 days.

This patent is subject to a terminal disclaimer.

(21) Appl. No.: 10/856,475

(22) Filed: May 28, 2004

(65) Prior Publication Data

US 2005/0033288 A1 Feb. 10, 2005
US 2007/0088355 A9 Apr. 19, 2007

Related U.S. Application Data

(63) Continuation-in-part of application No. 10/754,790, filed on Jan. 8, 2004, now Pat. No. 8,021,359.

(60) Provisional application No. 60/474,055, filed on May 28, 2003, provisional application No. 60/447,760, filed on Feb. 13, 2003.

(51) Int. Cl.
*A61B 18/14* (2006.01)

(52) U.S. Cl. .............. 606/41; 606/27; 606/213
(58) Field of Classification Search .............. 606/41, 606/48–50, 213–215
See application file for complete search history.

(56) References Cited

U.S. PATENT DOCUMENTS

| | | | |
|---|---|---|---|
| 2,582,628 A * | 1/1952 | Halloran | |
| 3,862,627 A | 1/1975 | Hans, Sr. | |
| 3,874,388 A * | 4/1975 | King et al. | 606/232 |
| 4,273,127 A | 6/1981 | Auth et al. | |
| 4,492,231 A | 1/1985 | Auth | |
| 4,532,924 A | 8/1985 | Auth et al. | |
| 4,556,065 A | 12/1985 | Hoffmann | |
| 4,799,479 A | 1/1989 | Spears | |
| 4,813,926 A | 3/1989 | Kerwin | |
| 4,822,348 A | 4/1989 | Casey | |
| 4,832,048 A | 5/1989 | Cohen | |
| 4,850,960 A | 7/1989 | Grayzel | |
| 4,892,098 A | 1/1990 | Sauer | |
| 4,929,246 A | 5/1990 | Sinofsky | |

(Continued)

FOREIGN PATENT DOCUMENTS

WO WO-87/04081 A1 7/1987

(Continued)

OTHER PUBLICATIONS

U.S. Appl. No. 11/004,634, Auth et al.*

(Continued)

*Primary Examiner* — Michael Peffley
(74) *Attorney, Agent, or Firm* — DLA Piper LLP (US)

(57) ABSTRACT

Methods, systems, and devices for transseptal access into the left atrium of a heart. In one embodiment an apparatus for transseptal left atrial access comprised of a catheter adapted for insertion into a vessel and one or more RF devices adapted to be extendable from the distal end of said catheter and configured for the penetration or sealing of septal tissue.

10 Claims, 3 Drawing Sheets

U.S. PATENT DOCUMENTS

| | | |
|---|---|---|
| 5,056,517 A | 10/1991 | Fenici |
| 5,071,417 A | 12/1991 | Sinofsky |
| 5,122,137 A | 6/1992 | Lennox |
| 5,156,613 A | 10/1992 | Sawyer |
| 5,207,670 A | 5/1993 | Sinofsky |
| 5,290,272 A | 3/1994 | Burstein et al. |
| 5,290,278 A | 3/1994 | Anderson |
| 5,298,224 A | 3/1994 | Plum |
| 5,300,065 A | 4/1994 | Anderson |
| 5,334,191 A | 8/1994 | Poppas et al. |
| 5,336,221 A | 8/1994 | Anderson |
| 5,364,389 A | 11/1994 | Anderson |
| 5,405,322 A | 4/1995 | Lennox et al. |
| 5,409,479 A | 4/1995 | Dew et al. |
| 5,409,481 A | 4/1995 | Poppas et al. |
| 5,421,338 A | 6/1995 | Crowley et al. |
| 5,451,235 A | 9/1995 | Lock et al. |
| 5,454,807 A | 10/1995 | Lennox et al. |
| 5,505,730 A | 4/1996 | Edwards |
| 5,507,744 A | 4/1996 | Tay et al. |
| 5,522,873 A | 6/1996 | Jackman et al. |
| 5,540,677 A | 7/1996 | Sinofsky |
| 5,545,195 A | 8/1996 | Lennox et al. |
| 5,569,239 A | 10/1996 | Sinofsky |
| 5,571,088 A | 11/1996 | Lennox et al. |
| 5,571,216 A | 11/1996 | Anderson |
| 5,575,772 A | 11/1996 | Lennox |
| 5,584,872 A | 12/1996 | LaFontaine et al. |
| 5,611,794 A | 3/1997 | Sauer et al. |
| 5,643,171 A | 7/1997 | Bradshaw et al. |
| 5,658,280 A | 8/1997 | Issa |
| 5,662,643 A | 9/1997 | Kung et al. |
| 5,662,647 A * | 9/1997 | Crow et al. ............... 606/41 |
| 5,669,934 A | 9/1997 | Sawyer |
| 5,687,723 A * | 11/1997 | Avitall ............... 600/374 |
| 5,695,493 A | 12/1997 | Nakajima et al. |
| 5,702,421 A | 12/1997 | Schneidt |
| 5,709,224 A | 1/1998 | Behl et al. |
| 5,713,891 A | 2/1998 | Poppas |
| 5,725,512 A | 3/1998 | Swartz et al. |
| 5,725,522 A | 3/1998 | Sinofsky |
| 5,725,552 A * | 3/1998 | Kotula et al. ............... 606/213 |
| 5,749,895 A | 5/1998 | Sawyer et al. |
| 5,757,772 A | 5/1998 | Thornberg et al. |
| 5,782,848 A | 7/1998 | Lennox |
| 5,782,860 A | 7/1998 | Epstein et al. |
| 5,810,810 A | 9/1998 | Tay et al. |
| 5,824,015 A | 10/1998 | Sawyer |
| 5,827,265 A | 10/1998 | Glinsky et al. |
| 5,827,268 A | 10/1998 | Laufer |
| 5,865,827 A | 2/1999 | Bullister |
| 5,868,702 A * | 2/1999 | Stevens et al. ............... 604/96.01 |
| 5,873,828 A | 2/1999 | Fujio et al. |
| 5,897,551 A | 4/1999 | Everett et al. |
| 5,919,188 A * | 7/1999 | Shearon et al. ............... 606/41 |
| 5,919,191 A | 7/1999 | Lennox et al. |
| 5,919,200 A | 7/1999 | Stambaugh et al. |
| 5,925,078 A | 7/1999 | Anderson |
| 5,928,224 A | 7/1999 | Laufer |
| 5,928,266 A | 7/1999 | Kontos |
| 5,931,165 A | 8/1999 | Reich et al. |
| 5,944,738 A * | 8/1999 | Amplatz et al. ............... 606/213 |
| 5,957,919 A | 9/1999 | Laufer |
| 5,964,782 A | 10/1999 | Lafontaine et al. |
| 5,972,026 A | 10/1999 | Laufer et al. |
| 5,984,909 A | 11/1999 | Lurie et al. |
| 5,989,284 A | 11/1999 | Laufer |
| 6,004,269 A | 12/1999 | Crowley et al. |
| 6,004,316 A | 12/1999 | Laufer |
| 6,010,516 A | 1/2000 | Hulka |
| 6,033,397 A | 3/2000 | Laufer et al. |
| 6,033,398 A | 3/2000 | Farley et al. |
| 6,036,687 A | 3/2000 | Laufer et al. |
| 6,048,333 A | 4/2000 | Lennox et al. |
| 6,063,081 A | 5/2000 | Mulier et al. |
| 6,063,085 A | 5/2000 | Tay et al. |
| 6,066,126 A | 5/2000 | Li et al. |
| 6,068,653 A | 5/2000 | LaFontaine |
| 6,071,277 A | 6/2000 | Farley et al. |
| 6,071,279 A * | 6/2000 | Whayne et al. ............... 606/41 |
| 6,071,303 A | 6/2000 | Laufer |
| 6,083,219 A | 7/2000 | Laufer |
| 6,083,223 A | 7/2000 | Baker |
| 6,083,255 A | 7/2000 | Laufer et al. |
| 6,086,586 A | 7/2000 | Hooven |
| 6,087,552 A | 7/2000 | Gregory |
| 6,091,995 A | 7/2000 | Ingle et al. |
| 6,106,520 A | 8/2000 | Laufer et al. |
| 6,128,522 A | 10/2000 | Acker et al. |
| 6,132,429 A | 10/2000 | Baker |
| 6,135,997 A | 10/2000 | Laufer et al. |
| 6,139,527 A | 10/2000 | Laufer et al. |
| 6,149,660 A | 11/2000 | Laufer et al. |
| 6,152,139 A | 11/2000 | Laufer |
| 6,156,032 A | 12/2000 | Lennox |
| 6,165,206 A | 12/2000 | Tu |
| 6,168,594 B1 | 1/2001 | LaFontaine et al. |
| 6,200,315 B1 | 3/2001 | Gaiser et al. |
| 6,200,333 B1 | 3/2001 | Laufer |
| 6,206,907 B1 | 3/2001 | Marino et al. |
| 6,210,411 B1 * | 4/2001 | Hofmann et al. ............... 606/52 |
| 6,211,335 B1 | 4/2001 | Owen et al. |
| 6,212,426 B1 * | 4/2001 | Swanson ............... 600/510 |
| 6,221,068 B1 | 4/2001 | Fried et al. |
| 6,223,087 B1 * | 4/2001 | Williams ............... 607/119 |
| 6,238,389 B1 | 5/2001 | Paddock et al. |
| 6,254,598 B1 | 7/2001 | Edwards et al. |
| 6,254,601 B1 | 7/2001 | Burbank et al. |
| 6,257,241 B1 | 7/2001 | Wampler |
| 6,258,087 B1 | 7/2001 | Edwards et al. |
| 6,273,886 B1 | 8/2001 | Edwards et al. |
| 6,273,907 B1 | 8/2001 | Laufer |
| 6,283,935 B1 | 9/2001 | Laufer et al. |
| 6,283,962 B1 | 9/2001 | Tu et al. |
| 6,283,988 B1 | 9/2001 | Laufer et al. |
| 6,283,989 B1 | 9/2001 | Laufer et al. |
| 6,290,674 B1 | 9/2001 | Roue et al. |
| 6,299,633 B1 | 10/2001 | Laufer |
| 6,302,898 B1 | 10/2001 | Edwards et al. |
| 6,323,037 B1 | 11/2001 | Lauto et al. |
| 6,325,798 B1 | 12/2001 | Edwards et al. |
| 6,338,731 B1 | 1/2002 | Laufer et al. |
| 6,352,534 B1 | 3/2002 | Paddock et al. |
| 6,355,030 B1 | 3/2002 | Aldrich et al. |
| 6,355,031 B1 | 3/2002 | Edwards et al. |
| 6,358,245 B1 | 3/2002 | Edwards et al. |
| 6,375,615 B1 | 4/2002 | Flaherty et al. |
| 6,379,368 B1 | 4/2002 | Corcoran et al. |
| 6,383,198 B1 | 5/2002 | Hamilton |
| 6,391,048 B1 | 5/2002 | Ginn et al. |
| 6,391,049 B1 | 5/2002 | McNally et al. |
| 6,398,779 B1 | 6/2002 | Buysse et al. |
| 6,398,782 B1 | 6/2002 | Pecor et al. |
| 6,398,797 B2 | 6/2002 | Bombard et al. |
| 6,401,719 B1 | 6/2002 | Farley et al. |
| 6,401,720 B1 * | 6/2002 | Stevens et al. ............... 128/898 |
| 6,419,669 B1 | 7/2002 | Frazier et al. |
| 6,438,424 B1 | 8/2002 | Knowlton |
| 6,440,128 B1 | 8/2002 | Edwards et al. |
| 6,440,152 B1 | 8/2002 | Gainor et al. |
| 6,453,202 B1 | 9/2002 | Knowlton |
| 6,461,314 B1 | 10/2002 | Pant et al. |
| 6,463,332 B1 | 10/2002 | Aldrich |
| 6,464,626 B1 | 10/2002 | Peterson |
| 6,464,689 B1 | 10/2002 | Qin et al. |
| 6,470,216 B1 | 10/2002 | Knowlton |
| 6,482,203 B2 | 11/2002 | Paddock et al. |
| 6,488,673 B1 | 12/2002 | Laufer et al. |
| 6,494,879 B2 | 12/2002 | Lennox et al. |
| 6,494,888 B1 | 12/2002 | Laufer et al. |
| 6,506,196 B1 | 1/2003 | Laufer |
| 6,520,185 B1 | 2/2003 | Bommannan et al. |
| 6,524,326 B1 | 2/2003 | Zhu et al. |
| 6,526,302 B2 | 2/2003 | Hassett |
| 6,529,778 B2 | 3/2003 | Prutchi |
| 6,547,776 B1 | 4/2003 | Gaiser et al. |
| 6,554,827 B2 | 4/2003 | Chandrasekaran et al. |

| | | |
|---|---|---|
| 6,558,366 B1 | 5/2003 | Drasler et al. |
| 6,562,034 B2 | 5/2003 | Edwards et al. |
| 6,562,037 B2 | 5/2003 | Paton et al. |
| 6,562,052 B2 | 5/2003 | Nobles et al. |
| 6,565,557 B1 | 5/2003 | Sporri et al. |
| 6,575,971 B2 | 6/2003 | Hauck et al. |
| 6,577,902 B1 | 6/2003 | Laufer et al. |
| 6,583,117 B2 | 6/2003 | Owen et al. |
| 6,589,238 B2 | 7/2003 | Edwards et al. |
| 6,595,934 B1 | 7/2003 | Hissong et al. |
| 6,602,251 B2 | 8/2003 | Burbank et al. |
| 6,605,084 B2 | 8/2003 | Acker et al. |
| 6,606,513 B2 | 8/2003 | Lardo et al. |
| 6,613,047 B2 | 9/2003 | Edwards |
| 6,629,534 B1 * | 10/2003 | St. Goar et al. ............... 128/898 |
| 6,629,951 B2 | 10/2003 | Laufer et al. |
| 6,635,052 B2 | 10/2003 | Loeb |
| 6,635,054 B2 | 10/2003 | Fjield et al. |
| 6,645,198 B1 | 11/2003 | Bommannan et al. |
| 6,663,622 B1 | 12/2003 | Foley et al. |
| 6,663,639 B1 | 12/2003 | Laufer et al. |
| 6,669,655 B1 | 12/2003 | Acker et al. |
| 6,669,687 B1 | 12/2003 | Saadat |
| 6,672,312 B2 | 1/2004 | Acker |
| 6,673,070 B2 | 1/2004 | Edwards et al. |
| 6,676,685 B2 | 1/2004 | Pedros et al. |
| 6,699,243 B2 | 3/2004 | West et al. |
| 6,702,835 B2 | 3/2004 | Ginn |
| 6,706,039 B2 | 3/2004 | Mulier et al. |
| 6,712,074 B2 | 3/2004 | Edwards et al. |
| 6,712,814 B2 | 3/2004 | Edwards et al. |
| 6,719,770 B2 | 4/2004 | Laufer et al. |
| 6,723,092 B2 | 4/2004 | Brown et al. |
| 6,728,565 B2 | 4/2004 | Wendlandt |
| 6,733,495 B1 | 5/2004 | Bek et al. |
| 6,733,498 B2 | 5/2004 | Paton et al. |
| 6,775,575 B2 | 8/2004 | Bommannan et al. |
| 6,776,784 B2 * | 8/2004 | Ginn ............................ 606/151 |
| 6,782,565 B2 | 8/2004 | Hinton |
| 6,783,523 B2 | 8/2004 | Qin et al. |
| 6,790,207 B2 | 9/2004 | Utley et al. |
| 6,802,841 B2 | 10/2004 | Utley et al. |
| 6,821,285 B2 | 11/2004 | Laufer et al. |
| 6,827,713 B2 | 12/2004 | Bek et al. |
| 6,836,688 B2 | 12/2004 | Ingle et al. |
| 6,852,108 B2 | 2/2005 | Barry et al. |
| 6,866,663 B2 | 3/2005 | Edwards et al. |
| 6,875,171 B2 | 4/2005 | Paolitto et al. |
| 6,887,238 B2 | 5/2005 | Jahns et al. |
| 6,939,348 B2 | 9/2005 | Malecki et al. |
| 2001/0051800 A1 * | 12/2001 | Eugeny et al. |
| 2002/0042564 A1 | 4/2002 | Cooper et al. |
| 2002/0068932 A1 * | 6/2002 | Edwards et al. |
| 2002/0082621 A1 | 6/2002 | Schurr et al. |
| 2002/0091379 A1 * | 7/2002 | Danek et al. |
| 2002/0095164 A1 | 7/2002 | Andreas et al. |
| 2002/0107512 A1 * | 8/2002 | Edwards |
| 2002/0107531 A1 | 8/2002 | Schreck et al. |
| 2002/0128672 A1 | 9/2002 | Dinger et al. |
| 2002/0143324 A1 | 10/2002 | Edwards |
| 2002/0151871 A1 | 10/2002 | Gaiser et al. |
| 2002/0169377 A1 * | 11/2002 | Khairkhahan et al. |
| 2002/0183787 A1 | 12/2002 | Wahr et al. |
| 2002/0183789 A1 | 12/2002 | Neev |
| 2002/0193787 A1 | 12/2002 | Qin et al. |
| 2002/0193816 A1 | 12/2002 | Laufer et al. |
| 2003/0009194 A1 * | 1/2003 | Saker et al. |
| 2003/0024538 A1 | 2/2003 | Edwards et al. |
| 2003/0028188 A1 | 2/2003 | Paddock et al. |
| 2003/0028189 A1 | 2/2003 | Woloszko et al. |
| 2003/0050632 A1 | 3/2003 | Fjield et al. |
| 2003/0069570 A1 * | 4/2003 | Witzel et al. |
| 2003/0078578 A1 | 4/2003 | Truckai et al. |
| 2003/0092689 A1 | 5/2003 | Escandon et al. |
| 2003/0093071 A1 | 5/2003 | Hauck et al. |
| 2003/0130730 A1 | 7/2003 | Cohn et al. |
| 2003/0135206 A1 | 7/2003 | Edwards et al. |
| 2003/0144652 A1 | 7/2003 | Baket et al. |
| 2003/0144694 A1 * | 7/2003 | Chanduszko et al. ........ 606/213 |
| 2003/0158551 A1 * | 8/2003 | Paton et al. |
| 2003/0178032 A1 | 9/2003 | Ingle et al. |
| 2003/0191511 A1 * | 10/2003 | Laufer et al. |
| 2003/0191512 A1 * | 10/2003 | Laufer et al. |
| 2003/0195511 A1 * | 10/2003 | Barry |
| 2003/0195593 A1 * | 10/2003 | Ingle et al. |
| 2003/0195604 A1 * | 10/2003 | Ingle et al. |
| 2003/0208232 A1 * | 11/2003 | Blaeser et al. |
| 2004/0003819 A1 * | 1/2004 | St. Goar et al. |
| 2004/0039312 A1 | 2/2004 | Hillstead et al. |
| 2004/0059347 A1 | 3/2004 | Hamilton |
| 2004/0143294 A1 * | 7/2004 | Corcoran et al. ............. 606/213 |
| 2004/0176752 A1 | 9/2004 | Alfano et al. |
| 2004/0193147 A1 * | 9/2004 | Malecki et al. ................. 606/32 |
| 2004/0230185 A1 | 11/2004 | Malecki et al. |
| 2004/0243122 A1 | 12/2004 | Auth et al. |
| 2004/0267191 A1 | 12/2004 | Gifford et al. |
| 2005/0015109 A1 * | 1/2005 | Lichtenstein ................. 606/200 |
| 2005/0021016 A1 * | 1/2005 | Malecki et al. ................. 606/27 |
| 2005/0034735 A1 | 2/2005 | Deem et al. |
| 2005/0055050 A1 | 3/2005 | Alfaro |
| 2005/0065506 A1 | 3/2005 | Phan |
| 2005/0070923 A1 | 3/2005 | McIntosh |
| 2005/0080406 A1 | 4/2005 | Malecki et al. |
| 2005/0119647 A1 * | 6/2005 | He et al. ......................... 606/41 |
| 2005/0131401 A1 | 6/2005 | Malecki et al. |
| 2005/0131460 A1 | 6/2005 | Gifford et al. |
| 2005/0192627 A1 | 9/2005 | Whisenant et al. |
| 2005/0192654 A1 * | 9/2005 | Chanduszko et al. ........ 607/116 |
| 2005/0228253 A1 | 10/2005 | Gifford et al. |
| 2005/0267464 A1 | 12/2005 | Truckai et al. |
| 2005/0267523 A1 | 12/2005 | Devellian et al. |
| 2005/0267524 A1 | 12/2005 | Chanduszko |
| 2005/0267525 A1 | 12/2005 | Chanduszko |
| 2005/0267526 A1 | 12/2005 | Wahr et al. |
| 2006/0009800 A1 | 1/2006 | Christianson et al. |
| 2006/0036282 A1 | 2/2006 | Wahr et al. |
| 2006/0036284 A1 | 2/2006 | Blaeser et al. |
| 2006/0074410 A1 | 4/2006 | Malecki et al. |

FOREIGN PATENT DOCUMENTS

| | | |
|---|---|---|
| WO | WO-97/32532 | 9/1997 |
| WO | WO-98/38936 | 9/1998 |
| WO | WO-99/18826 | 4/1999 |
| WO | WO-99/18862 | 4/1999 |
| WO | WO-99/18864 | 4/1999 |
| WO | WO-99/18870 | 4/1999 |
| WO | WO-99/18871 | 4/1999 |
| WO | WO-99/32040 | 7/1999 |
| WO | WO-99/34741 | 7/1999 |
| WO | WO-99/42044 | 8/1999 |
| WO | WO-99/42045 | 8/1999 |
| WO | WO-00/18307 | 4/2000 |
| WO | WO-00/18308 | 4/2000 |
| WO | WO-00/51510 | 9/2000 |
| WO | WO-00/57495 | 9/2000 |
| WO | WO-00/64387 | 11/2000 |
| WO | WO-00/66006 | 11/2000 |
| WO | WO-00/66015 | 11/2000 |
| WO | WO-00/66018 | 11/2000 |
| WO | WO-00/66019 | 11/2000 |
| WO | WO-00/66021 | 11/2000 |
| WO | WO-00/66052 | 11/2000 |
| WO | WO-01/10314 | 2/2001 |
| WO | WO-01/17450 | 3/2001 |
| WO | WO-02/24092 | 3/2002 |
| WO | WO-02/058780 | 8/2002 |
| WO | WO-02/060523 A2 | 8/2002 |
| WO | WO-02/060523 A3 | 8/2002 |
| WO | WO-02/067798 | 9/2002 |
| WO | WO-2004/043266 A2 | 5/2004 |
| WO | WO-2004/069055 A2 | 8/2004 |

OTHER PUBLICATIONS

U.S. Appl. No. 11/243,324, Barry.*
U.S. Appl. No. 60/474,055, Auth et al.
U.S. Appl. No. 60/477,760, Auth et al.
Caceci, Dr. Thomas, Text on Skeletal Muscle and Collagen Remodeling (10 Pages).

Chapter 6: Percutaneous Closure of Heart Defects, 2002, Health Research International (3 Pages).

Chatterjee, T. et al., "Nonsurgical Closure of Secundum Atrial Septal Defect and Patent Foremen Ovale," J Clin Basic Cardiol 4:35, 2001, Bern, Switzerland (4 Pgs.).

ConMed Corporation, "Suction Instruments & Tubing," (6 Pgs.).

Gifford, H. et al., "Methods and Apparatus for Treatment of patent Foramen Ovale," http://www.freshpatents.com/Methods-and-apparatus-for-treatment-of-patent-foramen-ovale-dt20050616ptan20050131460.php, Internet pp. 1-2, Jul. 18,2005.

Harper, R. et al., "Closure of Secundum Atrial Septal Defects With the Amplatzer Septal Occluder Device: Techniques and Problems," Catheterization and Cardiovascular Interventions, 2002, pp. 508-524, vol. 57, Wiley-Liss, Inc.

Johnston, J. H. et al., "Experimental Comparison of Endoscopic Yttrium-Aluminum-Garnet Laser, Electrosurgery, and Heater Probe for Canine Gut Arterial Coagulation: Importance of Compression and Avoidance of Erosion," Gastroenterology, 1987, pp. 1101-1108, vol. 92, No. 5, American Gastroenterological Association.

Karttunen, V. et al., "Ear Oximetry: A Noninvasive Method for Detection of Patent Foramen Ovale, A Study Comparing Dye Dilution Method and Oximetry With Contrast Transesophageal Echocardiography," Stroke, Feb. 2001, vol. 32, pp. 448-453, American Heart Association, Inc.

Kerut, E. et al., "Patent Foramen Ovale: A Review of Associated Conditions and the Impact of Physiological Size," Journal of the American College of Cardiology, Sep. 2001, pp. 613-623, vol. 38, No. 3, Elsevier Science, Inc.

Knebel, F., "Percutaneous Closure of Interatrial Communications in Adults-Prospective Embolism Prevention Study With Two and Three Dimensional Echocardiography," Cardiovascular Ultrasound, May 19, 2004, 2:5, (10 Pages).

Kramer, P., "The Hidden Connection," Endovascular Today, May 2004, pp. 47-52.

Lipton, R. et al., "Epidemiology and Economic Impact of Migraine," www.medscape.com/viewarticle/429665 <http://www.medscape.com/viewarticle/429665>, Curr Med Res Opin, 2001, 17(1s):s4-s12, Medscape.

Madison Skin & Laser Center, Thermalift™ Pre-Treatment Instructions & Thermalift™ Discharge Instructions. (2 Pages).

Malecki, W. et al., "Energy Based Devices and Methods for Treatment of Anatomic Tissue Defects," http://www.freshpatents.com/Energy-based-devices-and-methods-for-treatment-of-anatomic-tissue-defects-dt20050616ptan20050131401.php, Internet pp. 1-2, Jul. 18, 2005.

Malis, L., "Electrosurgery," J. Neurosurg., Nov. 1996, pp. 970-975, vol. 85.

Marshall, A. et al., "Structural and Compliant Anatomy of the Patent Foramen Ovale in Patients Undergoing Transcatheter Closure," American Heart Journal, Aug. 2000, pp. 303-307, vol. 140, No. 2, © Mosby, Inc.

Mayo Clinic, "Patent foremen Ovale: Paradoxical Embolism and Paradoxical Data," Mayo Clinic Proceedings, Jan. 2004, pp. 15-20, vol. 79, No. 1, Mayo Foundation for Medical Education and Research.

McClurken, M. et al., "Collagen Shrinkage and Vessel Sealing," TissueLink Medical, Inc., Technical Brief #300, TissueLink, Dover, NH.

McClurken, M. et al., "Thermal Effect of Tissue Link™ Technology on liver," TissueLink Medical, Inc., Technical Brief #301, TissueLink, Dover, NH.

McMahon, C.J. et al., "Use of the Transseptal Puncture in Transcatherer Closure of Long Tunnel-Type Patent Foramen Ovale," Heart, Aug. 2002, 88:e3, (2 Pages).

Meier, B. et al., "Contemporary Management of Patent Foramen Ovale," Circulation, Jan. 7-14, 2003, pp. 5-9, American Heart Association.

Meier, B., "Patent Foramen Ovale-Bearty Spot or Health Threat," CardiologyRounds, pp. 1-8, vol. 5, Issue 10, Dec. 2001, Brigham and Women's Hospital, Boston, Massachusetts.

Nkomo, V., et al. "Patent Foramen Ovale Transcatheter Closure Device Thromboisis," Mayo Clin Proc., Oct. 2001, pp. 1057-1061, vol. 76, © Mayo Foundation for Medical Education and Research.

NMT Medical, Inc. Brochure, "Cardioseal Septal Occlusion Systems," ML-0038.00, www.nmtmedical.com <http://www.nmtmedical.com> Boston MA (2 Pages).

NMT Medical, Inc. Brochure, "PFO Closure: Outcomes and Device Design Frequesently Asked Questions," ML-0116.00, pp. 1-4, www.nmtmedical.com <http://www.nmtmedical.com>, Boston, MA.

Overell, J.R. et al., "Interatrial Septal Abnormabilites and Stroke," Neurology, Oct. (2 of 2), 2000, vol. 55, pp. 1172-1179, ©AAN Enterprises.

Patent Foramen Ovale [PFO], (1 Page).

Rosenbaum, M. et al., "An Exploratory Investigation of the Morphology and Biochemistry of Cellulite," Journal of the American Society of Plastic Surgeons, Jun. 1993, pp. 1934-1939, vol. 101, Issue 7, Lippincott,Willams & Wilkins. (*Abstract Provided*-2 Pages ).

Ruiz, C. et al., "The Puncture Technique: A New Method for Transcatheter Closure of Patent Foramen Ovale," Catheterization and Cardiovascular Interventions, 2001, pp. 369-372, vol. 53, Wiley-Liss, Inc.

Schuchlenz, H. et al., "Transesophageal Echocardiography for Quantifying Size of Patent Foramen Ovale in patients With Cryptogenic Cerebrovascular Events," Stroke, Jan. 2003, p. 293-296, American Heart Association.

Schwerzmann, M. et al., "Percutaneous Closure of Patent Foramen Ovale Reduces the Frequency of Migraine Attacks," Neurology, Apr. (2 of 2), 2004, pp. 1399-1401, vol. 62, AAN Enterprises, Inc.

Shepard, S., "TissueLink's Hemostasis Device Stirs Interest of Local Surgeons," TissueLink, Nov. 7, 2003, Print Edition (3 Pages).

Silverglide, Surgical Technologies, inc., "What Makes SILVERGlide Non-Stick Bipolar Forceps Different." (1 Page).

Stuart, M., "Stroke Prevention: The Newest Frontier in Interventional Cardiology," Interventional Cardiology, Oct. 2003, p. 23-28, Windhover Information Inc.

Szili-Torok, T. et al., "Transseptal Left Heart Catheterisation Guided by Intracardiac Echocardiography," Heart, 2001, 86:e11, Dept. of Cardiology, Rotterdam, The Netherlands. (5 Pages).

The Thermage Procedure Brochure. (2 Pages).

Walsh, K.P. et al., "Transcatheter closure of patent foramen ovale Using the Amplatzer Septal Occluder to Prevent Recurrence of Neurological Decompression Illness in Divers," Heart 1999, pp. 257-261, vol. 81.

Wright, N. et al., "Denaturation of Collagen via Heating: An Irreversible Rate Process," Annual Review of Biomedical Engineering, 2002, pp. 109-128, vol. 4.

U.S. Appl. No. 60/458,854, Gifford.

U.S. Appl. No. 60/478,035, Gifford et al.

U.S. Appl. No. 60/490,082, Daem et al.

* cited by examiner

TRANSSEPTAL LEFT ATRIAL ACCESS AND SEPTAL CLOSURE

CROSS-REFERENCE TO RELATED APPLICATIONS

The present application claims priority to U.S. Provisional Application No. 60/474,055, filed May 28, 2003, and is a continuation-in-part of U.S. application Ser. No. 10/754,790, filed Jan. 8, 2004 now U.S. Pat. No. 8,021,359, which claims priority to U.S. Provisional Application No. 60/474,055, filed May 28, 2003, and U.S. Provisional Application No. 60/447,760, filed Feb. 13, 2003.

COPYRIGHT NOTICE

A portion of this patent document contains material that is subject to copyright protection. The copyright owner does not object to the facsimile reproduction of the patent document as it appears in the U.S. Patent and Trademark Office patent file or records but otherwise reserves all copyright rights whatsoever.

FIELD OF THE INVENTION

The present invention relates generally to the medical arts and specifically to transseptal methods, devices, and systems for accessing the left atrium of a patient's heart and for sealing closed an opening in the septum and/or for sealing septal tissue together.

BACKGROUND OF THE INVENTION

With recent advances in the cardiovascular arts, there's a renewed interest in finding safe and uncomplicated methods for accessing the left atrium of a patient's heart. Currently, a retrograde transaortal technique is most often and involves advancing a catheter through the aorta, into the left ventricle, accessing the left atrium from the left ventricle. However, this path into the left atrium is tortuous. A simple and more attractive alternative is accessing the left atrium directly from the right atrium by crossing the interatrial septum ("septum") that divides the two atrial chambers of the heart. The right atrium can be easily accessed and crossing the septum is the only requirement to entering the left atrium.

The left atrium can be accessed by puncturing across the septum of the heart at the fossa ovalis membrane, typically the thinnest part of the septum, with a needle-like device such as a Brockenbough needle. While this technique has been widely known since the 1950's, it has not been used largely because the technique has not proven reliable or secure. Misalignment or the incorrect orientation of the needle against the septum, for example, may have severe consequences for the patient, including perforation of the left atrium of the heart or perforation of a patient's aorta. Inadvertent perforations of the inferior vena cava and the coronary sinus have also been reported as a possible complication of this technique. Therefore, rapid, precise and controlled methods and devices for crossing the interatrial septum are needed. The present invention meets these, as well as other, needs.

SUMMARY OF THE INVENTION

Broadly, the invention is directed at methods and radiofrequency (RF) devices for crossing an interatrial septum and sealing an opening in it closed.

In yet another aspect of the invention, methods, RF systems and devices for sealing septal tissue are provided.

In yet another aspect of the invention, methods, RF systems, and devices for sealing closed an naturally occurring opening in a heart is a provided.

These, as well as other additional embodiments and features of the invention, will appear in the following description in conjunction with the accompanying drawings.

DESCRIPTION OF THE EMBODIMENTS

Figure 1A:
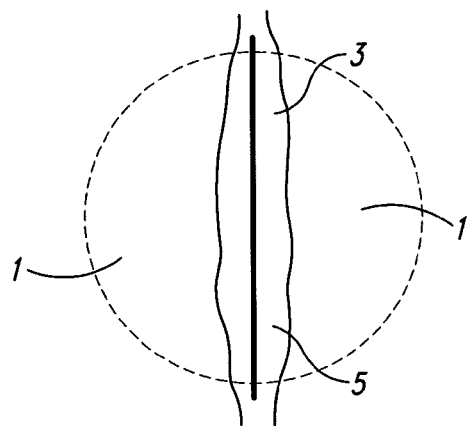
FIGS. 1A-1C are schematics illustrating the types of opening and closure patterns that can be created in the interatrial septum in accordance with the present invention.
Figure 1B:
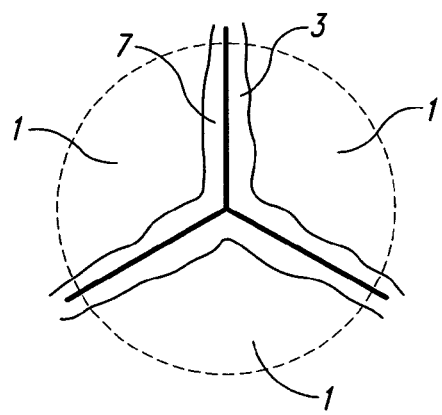
Figure 1C:
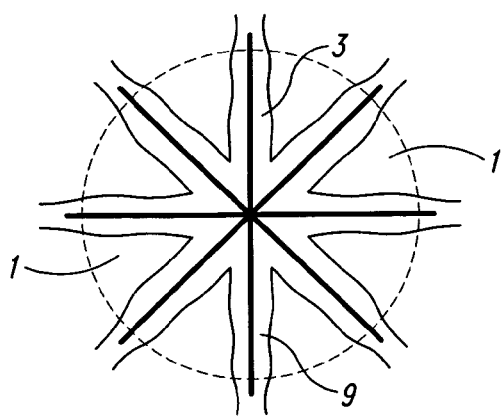

Broadly, methods, systems and RF devices for crossing the septum 1 and creating openings 3 of a specified size and pattern are provided. Methods, systems and RF devices for closing these openings 3 and joining septal tissue are also provided. Openings 3 in a wide variety of patterns and sizes can be created in the septum 1 in accordance with the present invention, including but not limited to: single slits 5 (FIG. 1A), radial slits 7 (FIG. 1B) and a plurality of bisecting slits 9 (FIG. 1C) as illustrated in FIGS. 1A-1C. The specific shape or pattern of the opening 3 is determined by the configuration of the wire(s) or electrodes(s) located on the distal end of an RF penetrating device or catheter as described herein. FIG. 1 further illustrates yet another aspect of the invention involving the use of an adaptively shaped RF sealing device or catheter to close the various types of openings 3. The dotted lines in FIG. 1 depict the shapes of various RF sealing devices or catheters that can be preferentially used to close septal openings 3 and join septal tissues 1 flaps together.

Figure 2:
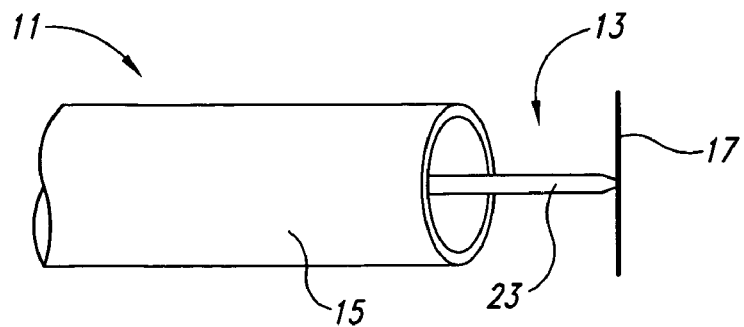
FIGS. 2-4 illustrate various embodiments of RF penetrating probes in accordance with the present invention.
Figure 3:
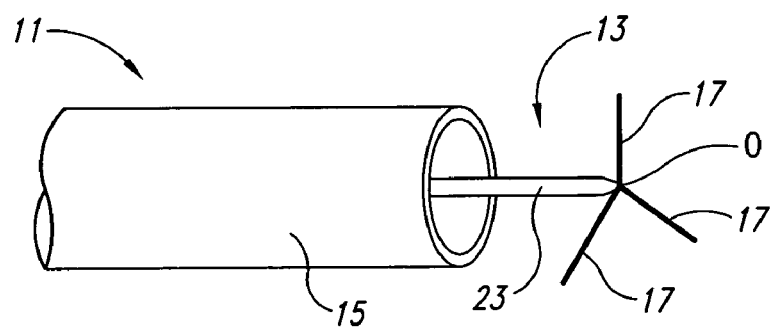
Figure 4:
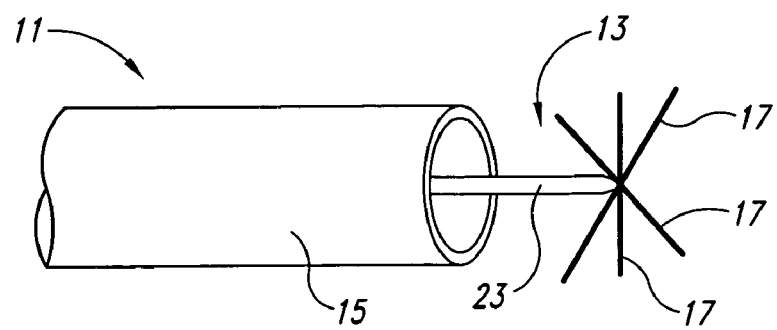

Turing now to the other figures, FIGS. 2, 3 and 4 illustrates various embodiments of RF penetrating devices 11. The various RF penetrating devices 11 are comprised of an RF penetrating probe 13 located at a distal end 15. The RF penetrating probe 13 is comprised of one or more wires 17 arranged in a particular shape. In a preferred embodiment, the RF penetrating probes 13 are made of shape memory wires 17 (such as Nitinol) to ensure the correct formation of the desired shape when the RF penetrating probe 13 is exposed inside the right atrium. The correct shape and orientation of the RF penetrating probe 13 and wires 17 against the septum 1 will determine the pattern of the opening 3 created in the septum 1 by the RF penetrating probe 13. When energized, the wires 17 or electrodes will supply sufficient RF energy to affect tissue penetration upon contact in the pattern dictated by the arrangement of the RF probe 13.

Each wire 17 of an RF penetrating probe 13 can be configured as a wire electrode, or in yet another implementation, each wire may be comprised of one or more spaced RF electrodes located within insulated shape memory wires. The electrodes of an RF penetrating probe 11 can be configured to operate as monopolar or bipolar electrodes delivering sufficient RF current to electrosurgically penetrate septal tissue 1 on contact. As will be readily appreciated by one skilled in the art, various strategies can be implemented to prevent sticking of tissues to the RF penetrating probes 13, wires 17 or electrodes described herein. In one possible implementation, various fluids or gels (either cooling and/or electrically conductive) may be used to prevent sticking of tissues during the penetration procedure. Yet another possible implementation may include a fluid (cooling or conductive) eluted from one or more ports located on a guide catheter. Alternatively, a fluid, coating or gel can be used on the RF probes 13, wires 17, or electrodes themselves to prevent tissue adhesion to the devices. In addition, one or more feedback sensors may be incorporated the present invention, preferably located adjacent to the RF penetration probes 13 to prevent unintended injury. The one or more feedback sensors can be configured to measure tissue impedances, temperatures, etc. as a means of preventing or controlling tissue heating, overheating or excessive tissue adhesion caused by heat generation.

FIG. 2 illustrates one embodiment of an RF penetration probe 13 for creating a slit-like opening 5 in the septum 1 of a patient's heart. As shown, the RF probe 13 comprises a relatively straight RF wire 17. RF wire 17 is attached to a connection member 23, which secures it to the distal end 15 of the RF penetration catheter 11. A described above, RF wire 17 can be configured as a wire electrode or can be comprised of a electrode located preferably in the middle of wires 17 wherein the ends of wire are insulated as illustrated. The size of the RF wire 17 or the electrode will depend on the desired size of the septal opening 3; if a longer slit 5 is desired a larger RF wires 17 or electrode may be employed. Though not illustrated, RF wire 17 is operationally connected by lead wires, or other like means, to an RF generator or energy source (not shown).

FIG. 3 illustrates yet another embodiment of an RF penetration probe 13. In this embodiment, RF penetration probe 13 is comprised of a plurality of wires 17 radiating from center point O. The wires 17 of the RF penetration probe 13, which are preferably straight, are secured to connection member at center point O. This RF penetration probe 13 illustrated in FIG. may be used to create the type of opening 7 depicted in FIG. 1B.

FIG. 4 illustrates yet another embodiment of the present invention wherein RF penetration probe 13 comprise a plurality of bisecting RF wires 17 that can be used to affect an opening 9 of the type illustrated in FIG. 1C. Each wire 17 in these embodiments may be configured as a wire electrode 17 or portions of the wire may be insulated 21.

Figure 5:
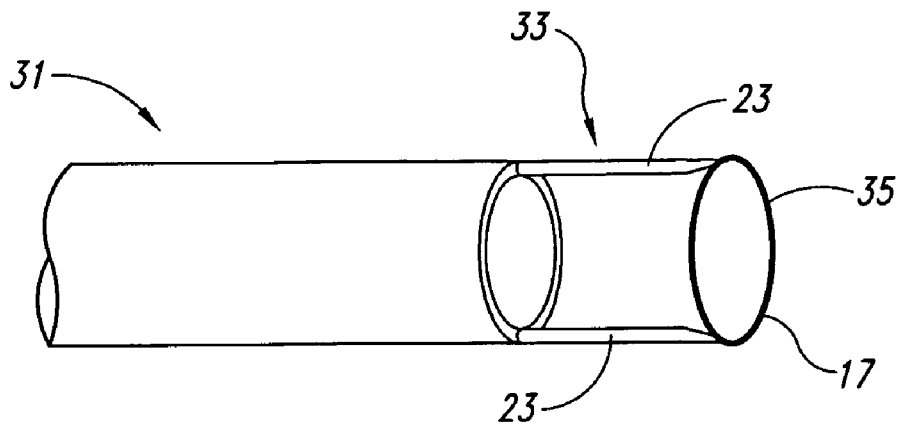
FIGS. 5-6 illustrate various embodiments of RF sealing probes in accordance with the present invention.
Figure 6:
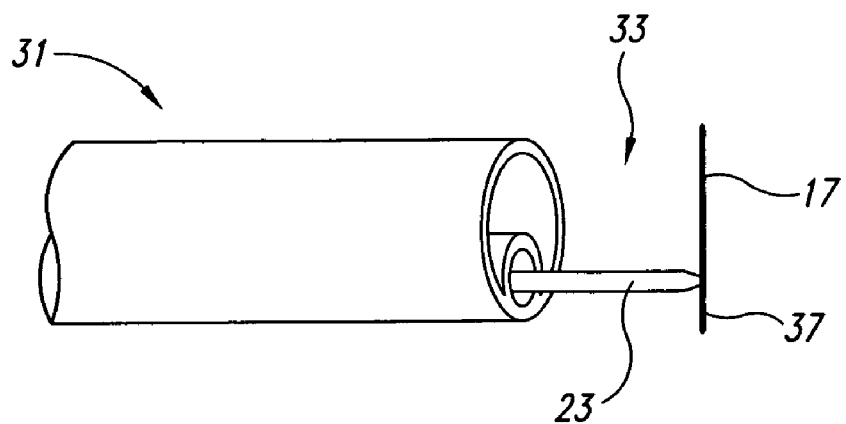

Turing to FIGS. 5 and 6, yet another aspect of the invention, is provided. In this aspect, various RF tissue sealing devices or catheters 31 comprising a distally located RF sealing probe 33, are illustrated. The RF sealing probe 33 is comprised of one or more wires 17 arranged in a pre-determined shape. Similar to the RF penetrating devices 11, the RF tissue sealing devices 31 can be configured as separate catheter device insertable into a guide catheter, or alternatively, can adapted to extend from the distal end of a guide catheter by use of a manipulator. For example, movement of a manipulator may control extension or retraction of both an RF penetrating device 11 and an RF sealing device 31 from the distal end of a guide catheter. To affect closure, RF wires 17, or electrodes of a RF sealing device 31, are configured to be operable at less intense modalities than the electrodes of an RF penetrating device 11 or probe 13. Specifically, the RF sealing probes 33 and the electrodes comprised therein are configured to heat, melt or coagulate tissues coming in contact with it. In addition, as provided in the art, heating of tissues at less intense parameters will trigger a healing response in the RF heated tissues, which will contribute and further promote closure of an opening and promote sealing of septal tissues.

Like the RF penetration probes 13, the RF sealing probes 33 of the present invention can be configured in a variety of shapes and sizes depending on the opening 3 to be closed. As illustrated in FIG, RF sealing probe 33 may be a circular wire 35 or a straight wire 37. Circular or straight type wires 35, 37 can be used to seal an opening 3 having several different patterns; for example, a circularly shaped RF sealing probe 35 can be used to seal a radial 7 or slit type 5 opening as illustrated in FIG. 1.

The various devices of the invention can be used similarly. The RF devices (including the tissue penetrating 11, 13 and sealing devices, catheters, probes 31, 33) can be delivered as a component of a catheter assembly system. The catheter assembly can comprise: a conventional guide or sheath catheter that can be introduced over a guidewire (not shown), an RF penetrating device 11 and/or an RF sealing device 31. First, the catheter assembly can be introduced into the right atrium from a number of access points using well known catheterization techniques. For example, to gain access to a patient's vasculature and the right atrium of the heart, commercially available introducers can be inserted into a vessel such as into the femoral vein or artery. The introducer can be of a variety of sizes, 4-14 French. The guide catheter should be readily insertable into an introducer and extend from the access point to the septum; this will require use of a guide catheter about 80-120 cm long and about 4-14 French. The guide catheter can be manufactured in accordance with a variety of known techniques, including as an extrusion of an appropriate material, such as high density polyethylenes (HDPE), polytetrafluoroethylenes, nylons, polyether-block amides, polyurethanes, polyimides, polyolefin copolyester and the like. However, other catheter materials well known in the catheter art, as well as various braiding techniques, may be employed depending on the desired catheter performance characteristics. In one embodiment, the guide catheter can be manufactured to be self-positioning to a desired location on a septum 3. For example, the guide catheter can be adapted so its distal tip preferentially locates to pre-determined position (such as at the fossa ovalis or above it), in which case the appropriate braiding technique can be used to affect preferential positioning of the distal tip of the catheter. Other component of the catheter assembly, in addition to a guide catheter, can include one or more of the following: an RF penetrating device 11, an RF sealing device 31, a guidewire, imaging components and the like. These components can be configured to be inserted into and extend out of the distal end of a guide catheter. Alternatively, these components, such as the RF devices 11, 31 can be configured to be extendable from the distal tip of guide catheter via a manipulator or other like means located at a proximal end of the guide catheter. In addition, these devices 11, 31 can be configured to extend only to pre-determined distances from the distal end of a guide catheter to ensure accurate penetration of the interatrial septum 1.

An RF penetrating device or catheter 5 can then be advanced into the guide catheter 43 and an RF penetrating probe 13 extended from its distal end. The RF penetration probe 43 should be placed into contact against the septum 1, and the electrodes energized to affect penetration. Pressure exerted on the proximal end of the RF penetration device or catheter 11 can used to ensure contact of septal tissue and the RF penetration probe 13. Other possible implementations include configuring the guide catheter to include a vacuum or suction port to help immobilize septal tissue against the RF penetration probe 13 during septal penetration.

Once a desired opening 3 has been created, the RF penetrating device or catheter 11 can be withdrawn from the guide catheter and replaced with other diagnostic or therapeutic devices or catheters. Once the left atrium has been sufficiently accessed and the other devices and catheters withdrawn, the closing or sealing procedure can be initiated using the RF sealing device or catheter 31 of the present invention. To affect closure or sealing of an atrial opening 3, a RF sealing probe 33 should be delivered into the right atrium and the RF wire or electrodes 17 energized. As previously described, activation of the RF sealing probe 33 will cause tissue and collagen melting, as well as coagulation, around the tissue flaps 1 of a septal opening 3. In addition, a heat-induced healing process, including scar formation and cell proliferation, will further contribute to of the septal closure and adhesion of the septal tissues.

As will be readily appreciated by one skilled in the art, the RF sealing devices and catheters 31 may be configured and used not only to seal actively created openings 3 but also those that occur naturally (ASDs, PFOs, floppy or aneurismal septums or PFOs). In one method of treatment, the distal end of an RF treatment catheter can be delivered adjacent an aneurismal or floppy PFO and RF energy applied to tighten the loose or septal tissue.

While this invention has been described in terms of specific embodiments, other embodiments will become apparent to those skilled in the art. Accordingly, the scope of the present invention is not intended to be limited by the specific embodiments disclosed herein, but rather, by the full scope of the claims.

We claim the following:

1. A method for treating an interatrial septum, the method comprising:
    moving an RF treatment device toward the septum from a right atrium of the heart;
    positioning a distal end of the RF treatment device having an RF electrode adjacent a treatment location, the treatment location being at the septum and external to any PFO;
    energizing the electrode;
    delivering sufficient energy to the treatment location to tighten the septum; and sealing an opening in the septum.

2. The method of claim 1 wherein sealing an opening includes sealing a naturally occurring PFO.

3. The method of claim 1, further comprising joining septal tissue flaps of the septum.

4. The method of claim 1, further comprising cooling the electrode.

5. The method of claim 1, further comprising at least reducing adhesion between the electrode and the septum with a fluid.

6. The method of claim 1, further comprising sensing a characteristic of the tissue.

7. The method of claim 1 wherein the electrode is one of multiple electrodes and wherein energizing the electrode includes energizing multiple electrodes.

8. The method of claim 1 wherein energizing the electrode includes energizing a wire-shaped electrode.

9. A method for treating an interatrial septum, the method comprising:
    moving an RF treatment device toward the septum from a right atrium of the heart;
    positioning a distal end of the RF treatment device having an RF electrode adjacent a treatment location, the treatment location being at the septum and external to a PFO;
    energizing the electrode; and
    delivering sufficient energy to the treatment location to tighten the septum.

10. A method of treating a patent foramen ovale in a heart, the method comprising:
    advancing a catheter device for treating the patent foramen ovale to a position in the heart which does not extend through the patent foramen ovale; and
    applying energy to tissues adjacent the patent foramen ovale with the catheter device to substantially close the patent foramen ovale.

* * * * *